(12) United States Patent
Sterin

(10) Patent No.: US 8,367,812 B2
(45) Date of Patent: *Feb. 5, 2013

(54) PREPARATION OF ORGANOSILICON COMPOUNDS

(75) Inventor: Sébastien Sterin, Saint Cyr Au Mont d'Or (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/921,019

(22) PCT Filed: May 16, 2006

(86) PCT No.: PCT/FR2006/001098
§ 371 (c)(1),
(2), (4) Date: Jan. 5, 2009

(87) PCT Pub. No.: WO2006/125884
PCT Pub. Date: Nov. 30, 2006

(65) Prior Publication Data
US 2009/0216000 A1    Aug. 27, 2009

(30) Foreign Application Priority Data
May 26, 2005 (FR) ...................................... 05 05283

(51) Int. Cl.
*C07F 7/18* (2006.01)
*C07F 7/10* (2006.01)

(52) U.S. Cl. ...................................................... 534/586

(58) Field of Classification Search ........................ None
See application file for complete search history.

(56) References Cited

U.S. PATENT DOCUMENTS

| 4,118,367 A | 10/1978 | Dawes et al. |
| 5,362,794 A * | 11/1994 | Inui et al. ....................... 524/496 |
| 5,380,828 A * | 1/1995 | Ravichandran et al. ....... 534/751 |

OTHER PUBLICATIONS

Mitchell, H. et al, "Animation of Arenes with Electron-Deficient Azodicarboxylates," J. Org. Chem., 1994, pp. 682-687, vol. 59.
Dawes, K et al., Chemical modification of natural rubber—a new silane coupling agent, Plastics and Rubber: Materials and Applications, Feb. 1978, pp. 24-25, XP0009060017, London, England.
Dawes, K et al., Chemical modification of natural rubber—a new silane coupling agent, RUBBERCON '77, 1977, pp. 18.1-18.11.
International Search Report, Oct. 13, 2006.

* cited by examiner

*Primary Examiner* — Fiona T Powers
(74) *Attorney, Agent, or Firm* — SNR Denton US LLP

(57) ABSTRACT

The synthesis of purified functionalized organosilicon compounds containing at least one active azo group having formula (I): $[(G^0)_3SiO_{1/2}]_m[(G^0)_2SiO_{2/2}]_n[G^0SiO_{3/2}]_o[SiO_{4/2}]_p[(G^2)_a(G^1)_a(Z-CO-HN=NH-CO-A)SiO_{(3-a-a')/2}]$ entails providing at least one hydrazino (—HN—NH—) precursor (II) of the compound (I) and oxidizing the precursor (II) into an azo group specific to the compound (I) with the aid of an oxidizing system comprising at least one oxidant (Ox) and at least one base (B), wherein 1) Ox is selected from among the oxidants that can oxidize a hydrazine function into an azo function, with or without the exclusion of N-bromosuccinimide (NBS), 2) and/or Ox (optionally B) is/are employed in stoichiometric quantities in relation to the precursor (II); 3) and/or the organosilicon compounds (I) thus prepared are subjected to a purification post-treatment to eliminate any unwanted residues of the base B used, with the proviso that, when NBS is not excluded, characteristic (1) is combined with characteristic (2) and/or characteristic (3).

14 Claims, No Drawings

PREPARATION OF ORGANOSILICON COMPOUNDS

CROSS-REFERENCE TO PRIORITY/PCT APPLICATIONS

This application claims priority under 35 U.S.C. §119 of FR 05/05283, filed May 26, 2005, and is a continuation of PCT/FR 2006/001098, filed May 16, 2006 and designating the United States (published in the French language on Nov. 30, 2006 as WO 2006/125884 A3; the title and abstract were also published in English), each hereby expressly incorporated by reference in its entirety and each assigned to the assignee hereof.

The field of the invention is the synthesis of functionalized organosilicon compounds.

The invention relates more particularly to organosilicon compounds comprising at least one activated azo group. Said activation can result, for example, from the presence of carbonyl groups near the nitrogens. The organosilicon moiety of these compounds can comprise for example hydrolyzable or condensable groups of type ≡SiOR or ≡SiOH.

Such organosilicon compounds with available activated azo group(s) (for example those with the group —CO—N=N—CO—) are very useful, notably in the synthesis of organic active molecules (for example nitrogen-containing heterocycles) for use in the areas of agrochemistry and pharmacy, for example as dienophiles in a hetero-Diels-Alder reaction.

However, few of these compounds are available, in particular because they are difficult to prepare. It would therefore be desirable to be able to extend the range of organosilicon compounds that are available.

In the sparse prior art, we find patent application FR-A-2340323, which discloses organosilicon compounds of formula (I*):

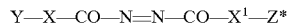

in which X and $X^1$, which may be identical or different, each represent an imino group, an oxygen atom or a substituted or unsubstituted methylene group; Y is a substituted or unsubstituted alkyl, aryl or aralkyl group, or is identical to Z*; Z* is an alkyl, aryl or aralkyl group with, as substituent, at least one silane group of formula $Si(OR)_3$ or $OSi(OR)_3$ in which R is a linear or branched alkyl group, preferably with 1 to 6 carbon atoms.

Organosilicon compounds of formula (II*) and (III*):

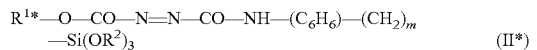

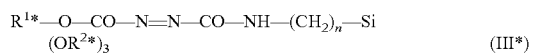

in which $R^{1*}$ and $R^{2*}$, which may be identical or different, each represent a linear or branched alkyl group preferably containing between 1 and 6 carbon atoms, m is equal to 0, 1, 2 or 3 and n is equal to 1, 2 or 3, are mentioned.

An organosilicon compound with azo groups of formula Ethyl-O—CO—N=N—CO—NH—(CH$_2$)$_3$—Si (OEthyl)$_3$, according to formula (III*), is disclosed in example 3.

The key stage in the synthesis of organosilicon compounds of this type with an activated azo group comprises the oxidation of a function of the hydrazo (NH—NH) type to a corresponding azo (N=N) function.

According to FR-A-2340323, this transformation is carried out by means of an oxidizing system comprising an oxidizing agent formed by a halogenated derivative (chlorine, bromine, N-bromosuccinimide among other examples) and a base of the pyridine type.

Thus, the method described in example 3 of FR-A-2340323 envisages the application of an organic solution of precursor Ethyl-O—CO—HN—NH—CO—NH—(CH$_2$)$_3$—Si(OEthyl)$_3$ and of pyridine, in dichloromethane. N-Bromosuccinimide (NBS) is added to this solution which is stirred for 2 hours after adding NBS. The solvent and the pyridine are removed by evaporation under vacuum, whereas the solid salts formed during the reaction are then removed by filtration. After washing the residue, the organosilicon compound with azo groups of formula (III*) is recovered in the filtrate. According to this document, the oxidizing system NBS-pyridine is used in excess (10 mol. %) relative to the precursor.

Finally, the end product is not pure. It contains residues that are undesirable and disadvantageous, notably in terms of industrial hygiene and of ecotoxicity on the one hand, and, on the other hand, in terms of performance in applications.

This known method has at least four drawbacks.

1. The use of solid NBS is a very disadvantageous operational factor in an industrial process.
2. This method leaves room for improvement in terms of yield and productivity.
3. This method is relatively expensive and would benefit from being improved in economic terms.
4. Finally, the quality of the final product (I*, II*, III*) obtained leaves something to be desired in particular with regard to purity and more precisely concerning the presence of undesirable pyridine residues in the final product. These residues are disadvantageous for the quality of the final product, notably on the one hand in terms of industrial hygiene and ecotoxicity, and on the other hand in terms of performance in applications of these functionalized organosilicon compounds, preferably with activated azo group(s).

In view of the prior art, one of the essential aims of the present invention is to propose an improved method of preparation of organosilicon compounds with azo group(s), by oxidation of the hydrazino group of a precursor to an azo group.

Another essential aim of the invention is to provide a method of preparation of organosilicon compounds with azo group(s), which avoids the use of solid reagents such as solid NBS, which make the method somewhat more complicated, notably for incorporation in the reaction mixture.

Another essential aim of the invention is to provide a method of preparation of organosilicon compounds with azo group(s), which offers better performance than those of the prior art, notably in terms of productivity and of yield of target azoalkoxysilane.

Another essential aim of the invention is to provide a method of preparation of organosilicon compounds with azo group(s), which is to be economical.

Another essential aim of the invention is to provide a method of preparation of organosilicon compounds with azo group(s), which would enable the quality of the final product to be optimized, notably with respect to the purity of organosilicon compounds and in particular by reducing to traces, or even completely eliminating undesirable residues of the base used, and notably pyridine residues when the base comprises pyridine. In doing so, the method is improved in terms of the quality of the final product, industrial hygiene and environmental impact.

Another essential aim of the present invention is to provide novel organosilicon compounds with azo group(s), with reduced content of pyridine residues.

These aims, among others, are achieved by the invention which relates, firstly, to a method of preparation of organosilicon compounds comprising one or more compounds, which may be identical to or different from one another, of formula (I) specified below:

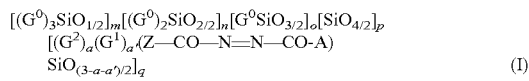

(I)

in which:
- m, n, o, p each represent an integer or fraction greater than or equal to 0;
- q represents an integer or fraction greater than or equal to 1;
- a represents an integer selected from 0, 1, 2 and 3;
- a' represents an integer selected from 0, 1 and 2;
- the sum a+a' is within the range from 0 to 3 with the conditions according to which:
    - -(C1)- when a=0, then:
        - either at least one of m, n, o, p is a number different from 0 (zero) and q is greater than or equal to 1;
        - or q is greater than 1 and each of m, n, o, p has any value,
        - and at least one of the symbols $G^0$ conforms to the definition given hereunder for $G^2$;
    - -(C2)- and when a+a'=3, then m=n=o=p=0 (zero);
- the symbols $G^0$, which may be identical or different, each represent one of the groups corresponding to $G^2$ or $G^1$;
- the symbols $G^2$, which may be identical or different, each represent: a hydroxyl group, a hydrolyzable monovalent group or two $G^2$ form together, and with the silicon to which they are attached, a ring having 3 to 5 hydrocarbon ring members and that can comprise at least one heteroatom, and at least one of said ring members can also be a ring member of at least one other hydrocarbon or aromatic ring;
- the symbols $G^1$, which may be identical or different, each represent: a saturated or unsaturated, aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;
- the symbol Z represents a divalent radical selected from: a saturated or unsaturated, aliphatic hydrocarbon group; a saturated, unsaturated and/or aromatic, monocyclic or polycyclic, carbocyclic group; and a group having a saturated or unsaturated, aliphatic hydrocarbon moiety and a carbocyclic moiety as defined above; said divalent radical being optionally substituted or interrupted by an oxygen atom and/or a sulfur atom and/or a nitrogen atom, said nitrogen atom bearing 1 monovalent group selected from: a hydrogen atom; a saturated or unsaturated, aliphatic hydrocarbon atom; a saturated or unsaturated and/or aromatic, monocyclic or polycyclic, carbocyclic group; and a group having a saturated or unsaturated aliphatic hydrocarbon moiety and a carbocyclic moiety as defined above;
- the symbol A represents:
    - a saturated or unsaturated, aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;
    - a group —X-$G^3$ where: X represents —O—, —S— or —$NG^4$- with $G^4$ having any one of the meanings given previously for $G^1$; $G^3$, which may be identical to or different from $G^4$, represents any one of the groups defined for $G^1$; and in addition the substituents $G^3$ and $G^4$ of the group —$NG^4G^3$ can form together, and with the nitrogen atom to which they are attached, a single ring having from 5 to 7 ring members, with the ring comprising 3 to 6 carbon atoms, 1 or 2 nitrogen atom(s) and optionally 1 or 2 unsaturated double bond(s);
- or, when q=1, a group [—Z—$SiO_{(3-a-a')/2}(G^2)_a(G^1)_{a'}$] [$(G^0)_3$ $SiO_{1/2}]_m[(G^0)_2SiO_{2/2}]_n[G^0SiO_{3/2}]_o[SiO_{4/2}]_p$ in which the symbols Z, $G^1$, $G^2$, a, a', m, n, o, and p have the definitions stated previously;

this method being of the type of those comprising
- employing at least one precursor (II) of at least one organosilicon compound (I), said precursor corresponding to the following formula (II):

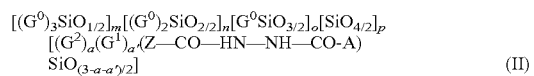

(II)

in which the symbols $G^0$, $G^0$, $G^2$, Z, A, m, n, o, p, a, a' and q are as defined above under formula (I),

- oxidizing the hydrazino group of precursor (II) to an azo group belonging to the organosilicon compound with activated azo group(s) (I), by means of an oxidizing system comprising at least one oxidizing agent (Ox) and at least one base (B), and, in the case when condition -(C1)- applies, employing an additional reagent selected from the silanes (used alone or as a mixture) of formula (III):

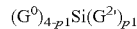

in which:
- the symbols $G^0$, which may be identical or different, each represent: a saturated or unsaturated, aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above; or a polysiloxane residue;
- the symbols $G^{2'}$, which may be identical or different, represent a hydrolyzable monovalent group corresponding to the same definition as was given above for the symbols $G^2$ described in relation to formula (I),
- p1 represents an integer selected from 1 and 2, preferably 1;

and said method being characterized in that:
1) Ox is selected from oxidizing agents that are able to oxidize a hydrazine function to an azo function, whether or not excluding N-bromosuccinimide (NBS), preferably from the halogens, halogen derivatives and mixtures thereof, and even more preferably from the group comprising: bromine, tert-butyl hypochlorite, trichloroisocyanuric acid, chlorine and mixtures thereof;
2) and/or Ox (optionally B) is (are) used in stoichiometric amounts relative to precursor (II);
3) and/or the organosilicon compounds (I) thus prepared undergo a post-treatment of purification which aims notably to remove any unwanted residues of the base B used;

with the condition that in the case when NBS is not excluded, characteristic 1) is combined with characteristic 2) and/or with characteristic 3).

The inventors have found an alternative to the NBS oxidizing reagents known in this type of reaction, without affecting the performance of the method (yield/productivity), nor the quality of the product, while allowing the method to become more economical.

Moreover, said compounds (I) obtained by the method according to the invention are remarkably pure. In particular, these compounds have little or no (undetectable traces) of undesirable residues derived, for example, from base B, such as pyridine residues when B comprises pyridine.

Without wishing to be bound to a theory, it is possible that this purity is at the origin of the excellent stability found for said compounds (I) resulting from the two-phase method according to the invention. By "stability" we mean notably stability in storage, especially in humid conditions, but in particular stability when heated.

According to an alternative or cumulative embodiment, it is envisaged to use a stoichiometric amount of Ox relative to precursor (II), whereas in the known method according to application FR-A-2340323 the oxidizing agent is in excess.

Preferably, Ox is selected from the halogens, the halogen derivatives and mixtures thereof, and even more preferably from the group comprising: bromine, tert-butyl hypochlorite, trichloroisocyanuric acid, chlorine and mixtures thereof.

According to a particular embodiment of the method according to the invention, a base B is used that comprises pyridine in stoichiometric amount relative to precursor (II). Said use of a limited amount of pyridine represents a significant advance relative to the prior art, for, as already explained above, pyridine forms undesirable residues that are very difficult to remove from the final organosilicon compounds (I).

According to an interesting embodiment, permitting optimization of the purity of the final target organosilicon compounds (I), a post-treatment is proposed in one or more stages, offering a significant improvement in quality of the final organosilicon compounds (I), contributing to the complete or almost complete removal of the undesirable residues arising, for example, from base B, in particular pyridine residues, which may be present when base B comprises pyridine. This post-treatment is all the more remarkable as it does not affect the yield and/or productivity with respect to the final organosilicon compounds (I).

The method according to the invention for the preparation of organosilicon compounds with an azo group (I) can be classed as a method of synthesis comprising at least the following stages:

(i): reacting a precursor silane of formula (IV):

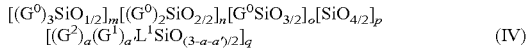

with a precursor hydrazo derivative of formula (V):

$L^2$-NH—NH—CO-A     (V)

formulas in which the symbols $G^0$, $G^1$, $G^2$, m, n, o, p, q, a, a' and A are as defined previously, and $L^1$ and $L^2$ represent groups whose structure and functionality are such that said groups are able to react with one another to give rise to the central linkage —Z—CO— to give the precursor of formula (II):

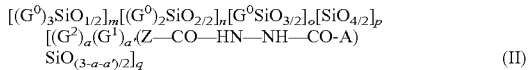

(ii): submitting the precursor of formula (II) to a reaction of oxidation of the hydrazo group —HN—NH— to an azo group —N=N—.

The oxidation in stage (ii) corresponds to the method of preparation according to the present invention.

For the preparation, for example, of organosilicon compounds with an azo group (I), in whose structure the symbol Z then represents the divalent radical —(CH$_2$)$_3$—NH—, the synthesis scheme that is employed can be as follows:

(i): react a precursor silane of formula (IV):

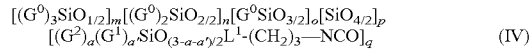

with a precursor hydrazo derivative of formula (V):

H$_2$N—NH—CO-A     (V)

to obtain the hydrazo compound of formula (II):

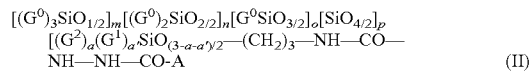

(ii): submit the compound of formula (II) to a reaction of oxidation of the hydrazo group —HN—NH— to an azo group —N=N—.

To summarize, stage (i) of obtaining the precursor (II) and stage (ii) of oxidation of (II) to (I) conform to the following general methodology:

Stage (i):
Use of a precursor hydrazo derivative of formula (V) and a solvent, at the ambient temperature in the reactor, under an inert atmosphere.
Stirring at several hundred rpm and heating at T=40-100° C.
Addition of the precursor silane of formula (IV) in several tens of minutes.
Reaction for several hours with stirring at T=40-100° C. before returning to room temperature.
Rest for several hours at room temperature.
Recovery of the precursor of formula (II) as a solid (for example), filtration, washing, drying.

Stage (ii):
Use of precursor (II), organic solvent, aqueous buffer and/or water and/or additive (A) at the ambient temperature in the reactor, under an inert atmosphere.
Addition of the oxidizing agent (Ox) and of (B$^0$), (B$^1$) to the reactor simultaneously, in small amounts (e.g. dropwise) and very slowly (a few minutes to several hours, e.g. in 0.5-2 h), at a temperature below 30° C., preferably at room temperature.
Stirring at room temperature for several hours.
Extraction of the aqueous phase and collection of the organic phase.
Separation of the organic phase.
Optionally drying.
Optionally filtration.
Concentration.
Recovery of the organosilicon compound with activated azo group (I).

Preferably, purification of the organosilicon compounds (I) is carried out by applying a post-treatment by which the content of impurities is reduced or even eliminated. Said impurities may originate for example from base B. Thus, when base B contains pyridine, pyridine residues may be formed, which are particularly undesirable from the standpoint of industrial hygiene and the performance of compounds (I) in applications.

Thus, according to a preferred embodiment of the invention, the post-treatment essentially comprises bringing the organosilicon compounds (I) in contact with a trap for impurities, said trap being selected:
from ionic-affinity supports, preferably from those belonging to the group comprising: carbon black;

and/or from chemical-affinity supports, preferably from those belonging to the group comprising: resins of an acidic nature.

Even more preferably, the post-treatment essentially comprises:

a) mixing an ionic-affinity support, preferably carbon black, with an organic solution of filling agent, at a rate of 0.1 to 20 wt. %, preferably at a rate of 1 to 10 wt. % of ionic-affinity support relative to the filling agent, b) leaving in contact preferably with stirring for a few minutes to several hours, c) separating the support loaded with impurities from the solution of filling agent, preferably by filtration, d) removing the solvent preferably by evaporation, e) mixing a chemical-affinity support, preferably a resin of acidic nature (advantageously a slightly acid resin of type IR50), with an organic solution of the filling agent, at a rate of 0.01 to 10 wt. %, preferably at a rate of 0.1 to 5 wt. % of chemical-affinity support relative to the filling agent, f) leaving in contact, preferably with stirring, for a few minutes to several hours, g) separating the support loaded with impurities from the solution of filling agent, preferably by filtration, h) removing the solvent preferably by evaporation.

and stages e) to h) can optionally be carried out before stages a) to d) or simultaneously.

In fact, stages a) to d) constitute a first treatment and stages e) to h) a second treatment, and these two treatments can be applied simultaneously or successively in any order.

Moreover, it is possible for the post-treatment used in the method according to the invention to comprise only one of these two treatments a) to d), on the one hand, and e) to h), on the other hand.

Apart from the general operating conditions described above, we should dwell a little longer on the organosilicon compounds with activated azo functional group(s) (I), obtained or that can be obtained by this method according to the invention.

As noted above, said compounds (I) are free or almost free (undetectable traces) of impurities, notably of pyridine residues. The invention therefore relates to organosilicon compounds with activated azo functional group(s) (I), as novel products, that can be obtained by the method according to the invention, characterized in that they are free or almost free (undetectable traces) of impurities, notably of pyridine residues.

Preferably, these novel organosilicon compounds (I) can be characterized by a content (wt. %) of pyridine residues less than or equal to 0.3, preferably to 0.2, and even more preferably to 0.1.

These organosilicon compounds with activated azo functional group(s) (I), which can be obtained by the method according to the invention, are also characterized in that they are stable when heated, e.g. at temperatures between 80 and 180°.

The invention also relates to the organosilicon compounds with activated azo functional group(s) (I), as novel products, characterized by a degree of hydrolysis/condensation (mol. %) of the functions $G^2$ less than or equal to 40, preferably to 10, and even more preferably to 1.

Moreover, in the following we shall return again to the meaning of the symbols in formula (I) above.

Firstly, it has to be understood that the group (Z—CO—N═N—CO-A) is joined to the Si atom of the $SiO_{(3-a-a')/2}$ unit via the divalent radical —Z—.

Moreover, aliphatic hydrocarbon group means, in the sense of the invention, a linear or branched group, preferably comprising from 1 to 25 carbon atoms, optionally substituted.

Advantageously, said aliphatic hydrocarbon group comprises from 1 to 18 carbon atoms, better still from 1 to 8 carbon atoms and even better still from 1 to 6 carbon atoms.

As saturated aliphatic hydrocarbon group, we may mention the alkyl groups, such as the methyl, ethyl, propyl, isopropyl, n-butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-dimethylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl and 7,7-dimethyloctyl, hexadecyl radicals.

The unsaturated aliphatic hydrocarbon groups comprise one or more unsaturations, preferably one, two or three unsaturations of the ethylenic type (double bond) and/or acetylenic type (triple bond).

Examples of them are the alkenyl or alkynyl groups derived from the alkyl groups defined above by elimination of two or more hydrogen atoms. Preferably, the unsaturated aliphatic hydrocarbon groups comprise a single unsaturation.

Within the scope of the invention, carbocyclic group means a monocyclic or polycyclic radical, optionally substituted, preferably of $C_3$-$C_{50}$. Advantageously, it is a $C_3$-$C_{18}$ radical, preferably mono-, bi- or tricyclic. When the carbocyclic group comprises more than one cyclic nucleus (as in the case of polycyclic carbocycles), the cyclic nuclei are condensed two by two. Two condensed nuclei can be orthocondensed or pericondensed.

The carbocyclic group can comprise, unless stated otherwise, a saturated moiety and/or an aromatic moiety and/or an unsaturated moiety.

Examples of saturated carbocyclic groups are the cycloalkyl groups. Preferably, the cycloalkyl groups are of $C_3$-$C_{18}$, and better still of $C_5$-$C_{10}$. We may notably mention the cyclopentyl, cyclohexyl, cycloheptyl, cyclooctyl, adamantyl or norbornyl radicals.

The unsaturated carbocycle or any unsaturated moiety of the carbocyclic type has one or more ethylenic unsaturations, preferably one, two or three. It has advantageously from 6 to 50 carbon atoms, and better still from 6 to 20, for example from 6 to 18. Examples of unsaturated carbocycles are the $C_6$-$C_{10}$ cycloalkenyl groups.

Examples of aromatic carbocyclic radicals are the ($C_6$-$C_{18}$) aryl groups, and better still ($C_6$-$C_{12}$)aryl and notably phenyl, naphthyl, anthryl and phenanthryl.

A group having both an aliphatic hydrocarbon moiety as defined above and a carbocyclic moiety as defined above is, for example, an aralkyl group such as benzyl, or an alkaryl group such as tolyl.

The substituents of the aliphatic hydrocarbon groups or moieties and of the carbocyclic groups or moieties are, for example, alkoxy groups in which the alkyl moiety is preferably as defined above.

By hydrolyzable monovalent group, as was discussed above in connection with the symbols $G^2$, we mean groups such as, for example: halogen atoms, notably chlorine; the groups —O-$G_7$ and —O—CO-$G_7$ where $G_7$ represents: a saturated or unsaturated, aliphatic hydrocarbon group, or a saturated, unsaturated and/or aromatic, monocyclic or polycyclic, carbocyclic group, or a group having a saturated or unsaturated, aliphatic hydrocarbon moiety and a carbocyclic moiety as defined above, and $G_7$ can optionally be halogenated and/or substituted with one or more alkoxy; the groups —O—N=CG$_8$G$_9$ in which G$_8$ and G$_9$ assume, independently, any one of the meanings given above for G$_7$, and G$_8$ and G$_9$ can be halogenated and/or optionally substituted with one or more alkoxy; the groups —O-NG$_8$G$_9$ in which G$_8$ and G$_9$ are as defined above.

Advantageously, said hydrolyzable monovalent group is a radical: $C_1$-$C_8$ alkoxy, linear or branched, optionally halogenated and/or optionally substituted with one or more ($C_1$-$C_8$) alkoxy; $C_2$-$C_9$ acyloxy optionally halogenated or optionally substituted with one or more ($C_1$-$C_8$)alkoxy; $C_5$-$C_{10}$ cycloalkyloxy; or $C_6$-$C_{18}$ aryloxy. As an example, the hydrolyzable group is methoxy, ethoxy, n-propoxy, isopropoxy, n-butoxy, methoxymethoxy, ethoxyethoxy, methoxyethoxy, β-chloropropoxy or β-chloroethoxy or alternatively acetoxy.

As monovalent carbocyclic groups that can be formed together, in formula (I), by two substituents G$^2$ and the silicon atom to which they are attached, we may mention for example the ring systems:

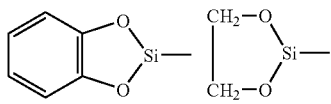

As single rings that can be formed together on the one hand by the substituents G$^3$ and G$^4$ of the nitrogen atom present in symbol A of formula (I) and on the other hand by the substituents R$^2$ and R$^3$ of the nitrogen atom present in symbol J of formula (III), we may mention for example the following rings where the free valence is carried by a nitrogen atom: pyrrole, imidazole, pyrazole, pyrrolidine, Δ2-pyrroline, imidazolidine, Δ2-imidazoline, pyrazolidine, Δ3-pyrazoline, piperidine; preferred examples are: pyrrole, imidazole and pyrazole.

In preferred forms F1 of formula (I):
the symbols G$^0$, which may be identical or different, correspond to the same definition as given hereunder for radicals G$^1$ or G$^2$;
the symbols G$_1$, which may be identical or different, each represent: a linear or branched $C_1$-$C_8$ alkyl radical; a $C_5$-$C_{10}$ cycloalkyl radical or a $C_6$-$C_{18}$ aryl radical;
the symbols G$_2$, which may be identical or different, each represent: a linear or branched $C_1$-$C_8$ alkoxy radical, optionally substituted with one or more ($C_1$-$C_8$)alkoxy;
Z represents the divalent radical Z'—Z"— where:
Z' represents: a $C_1$-$C_8$ alkylene chain; a $C_5$-$C_{10}$ saturated cycloalkylene group; a $C_6$-$C_{18}$ arylene group; or a divalent group comprising a combination of at least two of these radicals;
Z" represents: —O— or —NR$^4$—, where R$^4$ is: a hydrogen atom; a linear or branched $C_1$-$C_8$ alkyl radical; a $C_5$-$C_{10}$ cycloalkyl radical; a $C_6$-$C_{18}$ aryl radical; or a ($C_6$-$C_{18}$)aryl-($C_1$-$C_8$)alkyl radical;
A denotes a group —O-G$^3$ or —NG$^4$G$^3$ where G$^3$ and G$^4$, which may be identical to or different from one another, each represent: a linear or branched $C_1$-$C_8$ alkyl radical; a $C_5$-$C_{10}$ cycloalkyl radical or a $C_6$-$C_{18}$ aryl radical.

In more preferred forms F2 of formula (I):
the symbols G$^0$, which may be identical or different, correspond to the same definition as that given hereunder for the radicals G$^1$ or G$^2$;
the symbols G$_1$, which may be identical or different, are selected from the group comprising the methyl, ethyl, propyl, isopropyl, cyclohexyl and phenyl radicals;
the symbols G$_2$, which may be identical or different, are selected from the group comprising the methoxy, ethoxy, n-propoxy, isopropoxy, n-butoxy, methoxymethoxy, ethoxyethoxy and methoxyethoxy radicals;
Z represents the divalent radical Z'—Z"— where:
Z' represents: a $C_1$-$C_8$ alkylene chain;
Z" represents: —O— or —NR$^4$—, with R$^4$ being selected from the group comprising: hydrogen, the methyl, ethyl, propyl, isopropyl, n-butyl, isobutyl, t-butyl, pentyl, hexyl, cyclohexyl, and benzyl radicals;
A denotes a group —O-G$^3$ or —NG$^4$G$^3$ where G$^3$ and G$^4$, which may be identical to or different from one another, are selected from the group comprising the methyl, ethyl, propyl, isopropyl, cyclohexyl and phenyl radicals.

In even more preferred forms F3 of formula (I):
the symbols G$^0$, which may be identical or different, each represent one of the radicals selected hereunder for G$^1$ or G$^2$;
the symbols G$_1$, which may be identical or different, are selected from the group comprising the methyl, ethyl, propyl, isopropyl, cyclohexyl and phenyl radicals;
the symbols G$_2$, which may be identical or different, are selected from the group comprising the methoxy, ethoxy, n-propoxy, isopropoxy and n-butoxy radicals;
Z represents the divalent radical Z'—Z"— where:
Z' is selected from the group comprising the methylene, ethylene and propylene divalent radicals;
Z" represents: —O— or —NR$^4$— with R$^4$ being a hydrogen atom;
A denotes a group —O-G$^3$ where G$^3$ is selected from the group comprising the methyl, ethyl, propyl, isopropyl, cyclohexyl and phenyl radicals.

According to an especially preferred embodiment, the functionalized organosilicon compounds of general formula (I) are selected from the group comprising the following species:
(i) functionalized organosilanes corresponding to formula (I) in which: a+a'=3; m=n=o=p=0 (zero); and q=1;
(2i) functionalized siloxane oligomers corresponding to formula (I) in which: a+a'=1 or 2; m is in the range from 1 to 2; n=p=o=0 (zero); and q=1;
(3i) mixtures of at least one species (i) and/or of at least one species (2i).

The siloxane oligomers (2i) constitute a subgroup of compounds of formula (I). This subgroup is derived from a group of compounds of formula (I) corresponding to condition -(C1)- of the method according to the invention, namely when a=0, then:
either at least one of m, n, o, p is a number different from 0 (zero) and q is greater than or equal to 1;
or q is greater than 1 and each of m, n, o, p has any value, and at least one of the symbols G$^0$ corresponds to the definition given hereunder for G$^2$.

To obtain said compounds (I) complying with condition -(C1)-, it is advisable to employ an additional reagent (III) during the corresponding oxidation.

The amount of additional reagent (III) employed is not critical, but it is preferable, according to the invention, for this amount, relative to precursor (II), to be at least 0.1M, preferably from at least 1M up to 100M or more and, even more preferably, should be between 1 and 10M.

An example of additional reagent (III) is trimethylethoxysilane.

Advantageously, species (2i) are subdivided into subspecies:
- (2i.1) functionalized siloxane oligomers corresponding to formula (I) in which: a+a'=2; m=1; n=p=o=0 (zero); and q=1;
- (2i.2) functionalized siloxane oligomers corresponding to formula (I) in which: a+a'=1; m=2; n=p=o=0 (zero); and q=1.

According to an interesting variant of the especially preferred embodiment, the functionalized organosilicon compounds of general formula (I) are selected from the group of the following (sub)species:
- (i) functionalized organosilanes corresponding to formula (I) in which: a+a'=3; m=n=o=p=0 (zero); and q=1;
- (2i.1) functionalized siloxane oligomers corresponding to formula (I) in which: a+a'=2; m=1; n=p=o=0 (zero); and q=1;
- (2i.2) functionalized siloxane oligomers corresponding to formula (I) in which: a+a'=1; m=2; n=p=o=0 (zero); and q=1;
- (3i) mixtures of at least one species (i) and/or of at least one subspecies (2i.1) and/or of at least one subspecies (2i.2).

Within this variant, functionalized organosilicon compounds of general formula (I) that are particularly preferred are those formed by a mixture (3i) of at least one species (i) and/or of at least one subspecies (2i.1) and/or of at least one subspecies (2i.2).

In practice, it is possible for the organosilicon compounds according to the invention to comprise at least one mixture (3i) including compounds (i) and/or (2i.1) and/or (2i.2) of formula (I) in which:
- the symbols $G^0$, which may be identical or different, correspond to the definitions given below for $G^1$, $G^2$;
- the symbols $G_1$, which may be identical or different, are selected from the group comprising the methyl, ethyl, propyl, isopropyl, cyclohexyl and phenyl radicals;
- the symbols $G_2$, which may be identical or different, are selected from the group comprising the methoxy, ethoxy, n-propoxy, isopropoxy and n-butoxy radicals;
- A denotes a group —O-$G^3$ where $G^3$ is selected from the group comprising the methyl, ethyl, propyl, isopropyl, cyclohexyl and phenyl radicals.
- Z represents the divalent radical Z'—$NR^4$— where:
  - Z' is selected from the group comprising the methylene, ethylene and propylene divalent radicals;
  - $R^4$ is a hydrogen atom.

The invention also relates to organosilicon compounds of general formula (I), which can be obtained by the method according to the invention, taken in themselves and selected from the group comprising the following species:
- (i) functionalized organosilanes corresponding to formula (I) in which: a+a'=3; m=n=o=p=0 (zero); and q=1, apart from, in the case when the species (i) are used on their own, the organosilicon compounds of formula (I*), (II*) or (III*) as defined above;
- (2i) functionalized siloxane oligomers corresponding to formula (I) in which: a+a'=1 or 2; m is in the range from 1 to 2; n=p=o=0 (zero); and q=1;
- (3i) mixtures of at least one species (i) and/or of at least one species (2i).

If no additional reagent (III) is used, the compounds produced are silanes of the species (i), or in other words those corresponding to the following formula (I'):

   (I')

in which
- a represents an integer selected from 1, 2 and 3;
- a' represents an integer selected from 0, 1 and 2;
- a+a'=3;
- the symbols $G_1$, $G_2$, Z and A correspond to the same definitions as were given above for the preferred-forms F1, F2 or F3.

Even more preferably, the silanes of formula (I) in which a represents an integer equal to 3 and the symbols $G_1$, $G_2$, Z and A correspond to the same definitions as those given above for the preferred form F3.

As examples of silanes (i) of formula (I') that are especially suitable, we may notably mention the species of type (i) where a=3, a'=0, m=n=o=p=0 and q=1, of formulas:

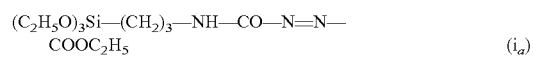 (i$_a$)

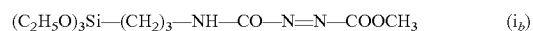 (i$_b$)

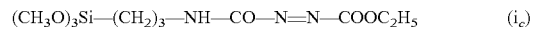 (i$_c$)

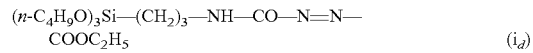 (i$_d$)

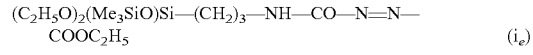 (i$_e$)

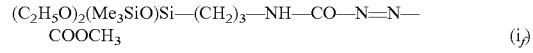 (i$_f$)

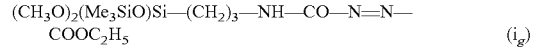 (i$_g$)

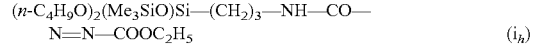 (i$_h$)

The invention will be better understood and its advantages will be seen more clearly from the examples given below, which illustrate the scope and the advantages of the method and of the novel products defined above.

These examples describe:
- Example 1: an embodiment where Ox=NBS, and Ox and B are used in stoichiometric amounts relative to precursor (II)
- Example 2: an embodiment where Ox=$Br_2$, and Ox is used in stoichiometric amount relative to precursor (II). B is used in stoichiometric amount relative to the HBr released
- Example 3: Post-treatment stages a) to d) then stages e) to h)

The above examples therefore show that:
- NBS and pyridine can be used in stoichiometric amounts relative to the precursor. This result is particularly interesting since excess pyridine is very difficult to remove from the medium.
- Bromine can advantageously replace NBS from the standpoint of cost even if its use means doubling the amount of pyridine (there is in this case twice as much hydrobromic acid to be trapped).
- A post-treatment in one or more stages can improve the quality of the final product by contributing to almost complete removal of the pyridine residues without deterioration of the Silcaf content of the sample.

EXAMPLE 1

Use of NBS/Pyridine Stoichiometric System

Load Materials:

| | | |
|---|---|---|
| Precursor (II) | 20.0 g | 57 mmol |
| Ox = N-Bromosuccinimide 99% | 10.13 g | 57 mmol |
| B = Pyridine | 4.5 g | 57 mmol |
| Solvent = Dichloromethane | 100 mL | / |

The precursor, the pyridine and the dichloromethane are loaded in a calibrated reactor with an argon atmosphere; the reaction mixture is homogeneous and practically colorless.

The N-bromosuccinimide (NBS) is added in 30 minutes by spatula. The temperature is kept below 25° C. Starting with the first addition of NBS, the reaction mixture becomes bright orange.

The reaction mixture is stirred at room temperature for 2 hours after the end of the addition of the NBS.

The reaction mixture is concentrated at reduced pressure in a rotary evaporator.

The residue, which is in the form of an orange paste, is taken up in 100 mL of a heptane/iPr$_2$O mixture (1/1:vol/vol) and then filtered on a glass frit (125 mL) of porosity 4. The filter cake is washed with additional 4×25 mL of the previous solvent mixture.

The mother liquor is filtered a second time on the cake. The filtrate is concentrated at reduced pressure.

An odorless, bright orange liquid is obtained: m=18.8 g. This liquid is analyzed by NMR (see Table 1).

EXAMPLE 2

Replacement of NBS with Bromine

Load Materials:

| | | |
|---|---|---|
| Precursor (II) | 10.0 g | 28.5 mmol |
| Ox = Bromine | 4.55 g | 28.5 mmol |
| B = Pyridine | 4.5 g | 57 mmol |
| Solvent = Dichloromethane | 60 mL | / |

The precursor, the pyridine and 45 mL of dichloromethane are loaded in a calibrated reactor under an argon atmosphere; the reaction mixture is homogeneous and practically colorless.

A solution of bromine in 15 mL of dichloromethane is poured into the reactor in 45 minutes. The temperature is kept below 25° C. During pouring of the bromine, the reaction mixture progressively assumes a bright orange hue.

The reaction mixture is stirred at room temperature for 2 hours after the end of pouring.

The reaction mixture is concentrated at reduced pressure in a rotary evaporator.

The residue, which is in the form of an orange paste, is taken up in 45 mL of a heptane/iPr$_2$O mixture (1/1:vol/vol) then filtered on a glass frit (125 mL) of porosity 4. The filter cake is washed with additional 2×10 mL of the previous solvent mixture.

The mother liquor is filtered a second time on the cake. The filtrate is concentrated at reduced pressure.

An odorless bright orange liquid is obtained: m=9.8 g.

TABLE 1

Comparative molar composition determined by NMR (mol. %)

| Example | Azoalkoxysilane (I) | Precursor (II) | Other impurities | Pyridine residues [i] |
|---|---|---|---|---|
| 1 | 94.5% | 0.2% | succinimide 5% | 0.35% |
| 2 | >96% | — | — | 0.2% |

[i] Mixture of pyridine and pyridinium hydrobromide

EXAMPLE 3

Removal of the Pyridine Residues

From the standpoint of industrial hygiene and ecotoxicity, the presence of pyridine residues is problematic. It is therefore particularly interesting to have samples containing a minimal amount of these compounds.

As the pyridine residues are made up of a mixture of pyridinium hydrobromide and pyridine, a double treatment has been envisaged:

1) with carbon black to adsorb impurities of the ionic type.
2) with a slightly acid resin (IR50 for example) dried beforehand for trapping the pyridine chemically.

Treatment with Carbon Black 2S is carried out according to the following operating procedure:

a) Dilution of the Silcaf in dichloromethane
b1) Addition of dry Carbon Black 2S at a rate of 6 wt. % relative to the Silcaf used
b2) Stirring for 2 hours at room temperature
c) Removal of the Carbon Black 2S by filtration
d) Evaporation of the solvent at reduced pressure (example 3 A)

The treatment with the resin is carried out according to the following operating procedure:

e) Dilution of the Silcaf in dichloromethane
f1) Addition of the dry resin at a rate of 2 wt. % relative to the Silcaf used
f2) Stirring for 2 hours at room temperature
g) Removal of the resin by filtration
h) Evaporation of the solvent at reduced pressure (example 3B)

TABLE 2

Variation in the nature and content of pyridine residues as a function of the treatment

| | Pyridine residues (mol) | | | | | |
|---|---|---|---|---|---|---|
| | Before treatment | | After treatment with Carbon Black 2S | | After treatments with resin IR50 | |
| Example | Nature | Content | Nature | Content | Nature | Content |
| 3.A | Mixture | 0.7% | Pyridine | 0.08% | / | / |
| 3.B | N.D. [i] | N.D. | Pyridine | 0.3% | N.D. | <<0.1% |

[i] N.D. = not determined

The above examples show that the treatment with Carbon Black 2S can remove the pyridinium hydrobromide, while the resin can trap the pyridine. Used consecutively, these two treatments therefore make it possible to obtain samples that are free or almost free of pyridine derivatives.

EXAMPLE 4

Synthesis of Precursor (II)

The synthetic route followed in the laboratory is described, though without examples, in many documents. It is shown schematically below.

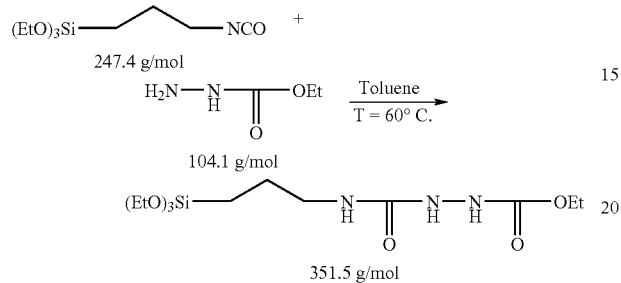

Load Materials

| | | |
|---|---|---|
| Isocyanatopropyltriethoxysilane at 96% (ABCR) [precursor silane (III)] | 99.8 g | 384 mmol |
| Ethyl carbazate [precursor hydrazo derivative (IV)] | 41.2 g | 384 mmol |
| Anhydrous Toluene (Aldrich) | 384 mL | / |

Procedure

The ethyl carbazate (IV) and the anhydrous toluene are loaded at the ambient temperature of the calibrated reactor, under an argon atmosphere.

The reactor is stirred at 300 rev/min and the reaction mixture RM is then heated to 60° C. (The RM becomes practically homogeneous when hot).

The 99.8 g of silane (III) is then added in 60 minutes using an isobaric pouring funnel.

The RM is stirred for 2 hours at 60° C. before returning to room temperature.

The RM is left to stand for some hours at room temperature.

A white solid crystallizes. It is filtered, washed with 2×150 mL of isopropyl ether and then dried under vacuum. The solid is finally stove-dried at 60° C. to constant weight. m=131.5 g.

The product constituting the precursor (II) is analyzed by NMR (molar purity>99%). Yield=97.4%.

The invention claimed is:

1. A method for the preparation of at least one organosilicon compound of the following formula (I):

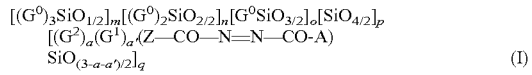
$$[(G^0)_3SiO_{1/2}]_m[(G^0)_2SiO_{2/2}]_n[G^0SiO_{3/2}]_o[SiO_{4/2}]_p$$
$$[(G^2)_a(G^1)_{a'}(Z-CO-N=N-CO-A)$$
$$SiO_{(3-a-a')/2}]_q \quad (I)$$

in which:
m, n, o, p each represent an integer or fraction greater than or equal to 0;
q is an integer or fraction greater than or equal to 1;
a is an integer selected from among 0, 1, 2 and 3;
a' is an integer selected from among 0, 1 and 2;
the sum a+a' ranges from 0 to 3, with the following conditions:

(C1) when a=0, then:
either at least one of m, n, o, p is a number different from 0 (zero) and q is greater than or equal to 1;
or q is greater than 1 and each of m, n, o, p has any value; and
at least one of the symbols $G^0$ has the definition given below for $G^2$;

(C2) and when a+a'=3, then m=n=o=p=0 (zero);

the symbols $G^0$, which may be identical or different, are each one of the groups $G^2$ or $G^1$;

the symbols $G^2$, which may be identical or different, are each: a hydroxyl group, a hydrolyzable monovalent group or two $G^2$ may together form, with the silicon atom from which they depend, a ring having 3 to 5 hydrocarbon ring members and which can also contain at least one heteroatom, and at least one of said ring members can also be a ring member of at least one other hydrocarbon or aromatic ring;

the symbols $G^1$, which may be identical or different, are each a saturated or unsaturated, aliphatic hydrocarbon group; a saturated, unsaturated or aromatic, monocyclic or polycyclic, carbocyclic group; or a saturated or unsaturated, aliphatic hydrocarbon moiety and a carbocyclic moiety as defined above;

the symbol Z is a divalent radical selected from the group consisting of a saturated or unsaturated, aliphatic hydrocarbon group; a saturated, unsaturated or aromatic, monocyclic or polycyclic carbocyclic group; and a group having a saturated or unsaturated aliphatic hydrocarbon moiety and a carbocyclic moiety as defined above; said divalent radical being optionally substituted or interrupted by an oxygen atom and/or a sulfur atom and/or a nitrogen atom, said nitrogen atom, when present, bearing 1 monovalent group selected from the group consisting of a hydrogen atom; a saturated or unsaturated aliphatic hydrocarbon group; a saturated or unsaturated and/or aromatic, monocyclic or polycyclic, carbocyclic group; and a group having a saturated or unsaturated, aliphatic hydrocarbon moiety and a carbocyclic moiety as defined above;

the symbol A is:
a saturated or unsaturated, aliphatic hydrocarbon group; a saturated, unsaturated or aromatic, monocyclic or polycyclic, carbocyclic group; or a group including a saturated or unsaturated, aliphatic hydrocarbon moiety and a carbocyclic moiety as defined above;
a group $—X-G^3$ wherein X is $—O—$, $—S—$ or $—NG^4-$ wherein $G^4$ has one of the above definitions for $G^1$; $G^3$, which may be identical to or different from $G^4$, is any one of the groups defined for $G^1$; the substituents $G^3$ and $G^4$ of the group $—NG^4G^3$ can together form, and with the nitrogen atom from which they depend, a single ring having from 5 to 7 ring members, containing in the ring 3 to 6 carbon atoms, 1 or 2 nitrogen atom(s) and optionally 1 or 2 unsaturated double bond(s);

or, when q=1, a group $[—Z—SiO_{(3-a-a')/2}(G^2)_a(G^1)_{a'}]$ $[(G^0)_3 SiO_{1/2}]_m[(G_0)_2SiO_{2/2}]_n[G^0SiO_{3/2}]_o[SiO_{4/2}]_p$ in which the symbols Z, $G^1$, $G^2$, a, a', m, n, o, and p are as defined above;

said method comprising:
(i) providing at least one precursor (II) of at least one organosilicon compound (I), said precursor having the following formula (II):

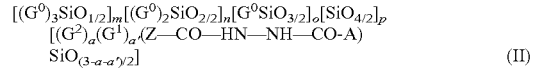
$$[(G^0)_3SiO_{1/2}]_m[(G^0)_2SiO_{2/2}]_n[G^0SiO_{3/2}]_o[SiO_{4/2}]_p$$
$$[(G^2)_a(G^1)_{a'}(Z-CO-HN-NH-CO-A)$$
$$SiO_{(3-a-a')/2}] \quad (II)$$

in which the symbols G⁰, G¹, G², Z, A, m, n, o, p, a, a' and q are as defined above under formula (I);

(ii) oxidizing the hydrazino group of said precursor (II) to an azo group belonging to the organosilicon compound with activated azo group(s) (I), by means of an oxidizing system comprising at least one oxidizing agent (Ox) and at least one base (B); and (iii) in the event that condition (C1) exists, employing an additional reagent selected from among the silanes (either alone or as a mixture) of formula (III):

(III)

in which:
the symbols $G^0$, which may be identical or different, are each a saturated or unsaturated, aliphatic hydrocarbon group; a saturated, unsaturated or aromatic, monocyclic or polycyclic, carbocyclic group; or a group including a saturated or unsaturated, aliphatic hydrocarbon moiety and a carbocyclic moiety as defined above; or a polysiloxane residue;

the symbols $G^{2'}$, which may be identical or different, are each a hydrolyzable monovalent group having the same definition as that given above for the symbols $G^2$ described in relation to formula (I);

p1 is an integer selected from 1 and 2;

wherein:
1) Ox is selected from the group consisting of bromine, tert-butyl hypochlorite, trichloroisocyanuric acid, chlorine, and mixtures thereof;
2) and/or Ox (optionally B) is (are) employed in stoichiometric amounts relative to precursor (II); and
3) and/or the organosilicon compounds (I) thus prepared are purified to remove any unwanted residues of the base B, the method further comprising purifying said organosilicon compounds (I) by contacting same with an impurities trap, such trap being selected:
from an ionic-affinity support; and/or
from a chemical-affinity support.

2. The method as defined by claim 1, comprising:
a. mixing an ionic-affinity support with an organic solution of filling agent, at a rate of 0.1 to 20 wt. % of ionic-affinity support relative to the filling agent,
b. maintaining same in contact optionally with stirring for a few minutes to several hours,
c. separating the support loaded with impurities from the solution of filling agent,
d. removing the solvent,
e. mixing a chemical-affinity support, optionally a resin of acidic nature with an organic solution of the filling agent, at a rate of 0.01 to 10 wt. % of chemical-affinity support relative to the filling agent,
f. maintaining same in contact optionally with stirring for a few minutes to several hours,
g. separating the support loaded with impurities from the solution of filling agent,
h. removing the solvent, and
optionally conducting said stages e) to h) before stages a) to d) or simultaneously.

3. The method as defined by claim 1, wherein formula (I):
the symbols $G^0$, which may be identical or different, have the same definition as that given hereunder for the radicals $G^1$ or $G^2$;
the symbols $G^1$, which may be identical or different, are each a linear or branched $C_1$-$C_8$ alkyl radical; a $C_5$-$C_{10}$ cycloalkyl radical or a $C_6$-$C_{18}$ aryl radical;

the symbols $G^2$, which may be identical or different, are each a linear or branched $C_1$-$C_8$ alkoxy radical, optionally substituted with one or more $C_1$-$C_8$ alkoxy radicals;
Z is the divalent radical Z'—Z"— wherein:
Z' is a $C_1$-$C_8$ alkylene radical; a $C_6$-$C_{10}$ saturated cycloalkylene radical; a $C_6$-$C_{18}$ arylene radical; or a divalent radical comprising a combination of at least two of these radicals;
Z" is —O— or —NR⁴—, wherein R⁴ is a hydrogen atom; a linear or branched $C_1$-$C_8$ alkyl radical; a $C_5$-$C_{10}$ cycloalkyl radical; a $C_6$-$C_{18}$ aryl radical or a ($C_6$-$C_{18}$) aryl-($C_1$-$C_8$)alkyl radical; and
A is a group —O-G³ or —NG⁴G³ wherein G³ and G⁴, which may be identical or different, are each a linear or branched $C_1$-$C_8$ alkyl radical; a $C_5$-$C_{10}$ cycloalkyl radical or a $C_6$-$C_{18}$ aryl radical.

4. The method as defined by claim 1, wherein formula (I):
the symbols $G^0$, which may be identical or different, have the same definition as that below for the radicals $G^1$ or $G^2$;
the symbols $G^1$, which may be identical or different, are each selected from the group consisting of the methyl, ethyl, propyl, isopropyl, cyclohexyl and phenyl radicals;
the symbols $G^2$, which may be identical or different, are each selected from the group consisting of the methoxy, ethoxy, n-propoxy, isopropoxy, n-butoxy, methoxymethoxy, ethoxyethoxy and methoxyethoxy radicals;
Z is the divalent radical Z'—Z"— wherein:
Z' is: a $C_1$-$C_8$ alkylene radical;
Z" is: —O— or —NR⁴—, wherein R⁴ is selected from the group consisting of hydrogen, the methyl, ethyl, propyl, isopropyl, n-butyl, isobutyl, t-butyl, pentyl, hexyl, cyclohexyl, and benzyl radicals;
A is a group —O-G³ or —NG⁴G³ wherein G³ and G⁴, which may be identical or different, are selected from the group consisting of the methyl, ethyl, propyl, isopropyl, cyclohexyl and phenyl radicals.

5. The method as defined by claim 1, wherein formula (I):
the symbols $G^0$, which may be identical or different, are each one of the radicals below for G' or $G^2$;
the symbols $G^1$, which may be identical or different, are each selected from the group consisting of the methyl, ethyl, propyl, isopropyl, cyclohexyl and phenyl radicals;
the symbols $G^2$, which may be identical or different, are each selected from the group consisting of the methoxy, ethoxy, n-propoxy, isopropoxy and n-butoxy radicals;
Z is the divalent radical Z'—Z"— wherein:
Z' is selected from the group consisting of the methylene, ethylene and propylene divalent radicals;
Z" is: —O— or —NR⁴— wherein R⁴ is a hydrogen atom;
A is a group —O-G³ wherein G³ is selected from the group consisting of the methyl, ethyl, propyl, isopropyl, cyclohexyl and phenyl radicals.

6. The method as defined by claim 1, wherein the compounds of formula (I) are selected from the group consisting of the following species:
(i) compounds corresponding to formula (I) in which: a+a'=3; m=n=o=p=0 (zero); and q=1;
(2i) compounds corresponding to formula (I) in which: a+a'=1 or 2; m is in the range from 1 to 2; n=p=o=0 (zero); and q=1;
(3i) mixtures of at least one species (i) and/or of at least one species (2i).

7. The method as defined by claim 1, wherein the compounds of formula (I) are selected from the group consisting of the following species:

(i) compounds corresponding to formula (I) in which: a+a'=3; m=n=o=p=0 (zero); and q=1;
(2i.1) compounds corresponding to formula (I) in which: a+a'=2; m=1; n=p=o=0 (zero); and q=1;
(2i.2) compounds corresponding to formula (I) in which: a+a'=1; m=2; n=p=o=0 (zero); and q=1;
(3i) mixtures of at least one species (i) and/or of at least one subspecies (2i.1) and/or of at least one subspecies (2i.2).

8. The method as defined by claim 1, wherein the compounds produced are those corresponding to the following formula (I'):

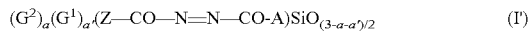

$(G^2)_a(G^1)_{a'}(Z-CO-N=N-CO-A)SiO_{(3-a-a')/2}$      (I')

in which:
a is an integer selected from 1, 2 and 3;
a' is an integer selected from 0, 1 and 2;
a+a'=3;
the symbols $G^1$, $G^2$, Z and A have the same definitions as those above.

9. The method as defined by claim 2, wherein formula (I):
the symbols $G^0$, which may be identical or different, have the same definition as that given hereunder for the radicals $G^1$ or $G^2$;
the symbols $G^1$, which may be identical or different, are each a linear or branched $C_1$-$C_8$ alkyl radical; a $C_5$-$C_{10}$ cycloalkyl radical or a $C_6$-$C_{18}$ aryl radical;
the symbols $G^2$, which may be identical or different, are each a linear or branched $C_1$-$C_8$ alkoxy radical, optionally substituted with one or more $C_1$-$C_8$ alkoxy radicals;
Z is the divalent radical Z'—Z"— wherein:
Z' is a $C_1$-$C_8$ alkylene radical; a $C_5$-$C_{10}$ saturated cycloalkylene radical; a $C_6$-$C_{18}$ arylene radical; or a divalent radical comprising a combination of at least two of these radicals;
Z" is —O— or —$NR^4$—, wherein $R^4$ is a hydrogen atom; a linear or branched $C_1$-$C_8$ alkyl radical; a $C_5$-$C_{10}$ cycloalkyl radical; a $C_6$-$C_{18}$ aryl radical or a ($C_8$-$C_{18}$) aryl-($C_1$-$C_8$)alkyl radical; and
A is a group —O-$G^3$ or —$NG^4G^3$ wherein $G^3$ and $G^4$, which may be identical or different, are each a linear or branched $C_1$-$C_8$ alkyl radical; a $C_5$-$C_{10}$ cycloalkyl radical or a $C_6$-$C_{18}$ aryl radical.

10. The method as defined by claim 2, wherein formula (I):
the symbols $G^0$, which may be identical or different, have the same definition as that below for the radicals $G^1$ or $G^2$;
the symbols $G^1$, which may be identical or different, are each selected from the group consisting of the methyl, ethyl, propyl, isopropyl, cyclohexyl and phenyl radicals;
the symbols $G^2$, which may be identical or different, are each selected from the group consisting of the methoxy, ethoxy, n-propoxy, isopropoxy, n-butoxy, methoxymethoxy, ethoxyethoxy and methoxyethoxy radicals;
Z is the divalent radical Z'—Z"— wherein:
Z' is: a $C_1$-$C_8$ alkylene radical;

Z" is: —O— or —$NR^4$—, wherein $R^4$ is selected from the group consisting of hydrogen, the methyl, ethyl, propyl, isopropyl, n-butyl, isobutyl, t-butyl, pentyl, hexyl, cyclohexyl, and benzyl radicals;
A is a group —O-$G^3$ or —$NG^4G^3$ wherein $G^3$ and $G^4$, which may be identical or different, are selected from the group consisting of the methyl, ethyl, propyl, isopropyl, cyclohexyl and phenyl radicals.

11. The method as defined by claim 2, wherein formula (I):
the symbols $G^0$, which may be identical or different, are each one of the radicals below for $G^1$ or $G^2$;
the symbols $G^1$, which may be identical or different, are each selected from the group consisting of the methyl, ethyl, propyl, isopropyl, cyclohexyl and phenyl radicals;
the symbols $G^2$, which may be identical or different, are each selected from the group consisting of the methoxy, ethoxy, n-propoxy, isopropoxy and n-butoxy radicals;
Z is the divalent radical Z'—Z"— wherein:
Z' is selected from the group consisting of the methylene, ethylene and propylene divalent radicals;
Z" is: —O— or —$NR^4$— wherein $R^4$ is a hydrogen atom;
A is a group —O-$G^3$ wherein $G^3$ is selected from the group consisting of the methyl, ethyl, propyl, isopropyl, cyclohexyl and phenyl radicals.

12. The method as defined by claim 2, wherein the compounds of formula (I) are selected from the group consisting of the following species:
(i) compounds corresponding to formula (I) in which: a+a'=3; m=n=o=p=0 (zero); and q=1;
(2i) compounds corresponding to formula (I) in which: a+a'=1 or 2; m is in the range from 1 to 2; n=p=o=0 (zero); and q=1;
(3i) mixtures of at least one species (i) and/or of at least one species (2i).

13. The method as defined by claim 2, wherein the compounds of formula (I) are selected from the group consisting of the following species:
(i) compounds corresponding to formula (I) in which: a+a'=3; m=n=o=p=0 (zero); and q=1;
(2i.1) compounds corresponding to formula (I) in which: a+a'=2; m=1; n=p=o=0 (zero); and q=1;
(2i.2) compounds corresponding to formula (I) in which: a+a'=1; m=2; n=p=o=0 (zero); and q=1;
(3i) mixtures of at least one species (i) and/or of at least one subspecies (2i.1) and/or of at least one subspecies (2i.2).

14. The method as defined by claim 2, wherein the compounds produced are those corresponding to the following formula (I'):

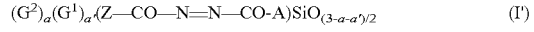

$(G^2)_a(G^1)_{a'}(Z-CO-N=N-CO-A)SiO_{(3-a-a')/2}$      (I')

in which:
a is an integer selected from 1, 2 and 3;
a' is an integer selected from 0, 1 and 2;
a+a'=3;
the symbols $G^1$, $G^2$, Z and A have the same definitions as in claim 2.

* * * * *